United States Patent
Dahlhaus et al.

(10) Patent No.: US 6,297,385 B1
(45) Date of Patent: Oct. 2, 2001

(54) ACETANILIDE COUPLERS

(75) Inventors: Uwe Dahlhaus, Burscheid; Hans Langen, Bonn; Heinz Wiesen, Euskirchen, all of (DE)

(73) Assignee: AGFA-Gevaert (BE)

( * ) Notice: Subject to any disclaimer, the term of this patent is extended or adjusted under 35 U.S.C. 154(b) by 0 days.

(21) Appl. No.: 09/449,071

(22) Filed: Nov. 24, 1999

(30) Foreign Application Priority Data

Dec. 3, 1998 (DE) ............................................. 198 55 808

(51) Int. Cl.$^7$ ................................................. C07D 349/12

(52) U.S. Cl. .......................................................... 548/264.2

(58) Field of Search ........................................... 548/264.4

(56) References Cited

FOREIGN PATENT DOCUMENTS 24 42 703  3/1976  (DE) .
1 529 573  10/1978  (GB) .

*Primary Examiner*—Patricia L. Morris
(74) *Attorney, Agent, or Firm*—Connolly Bove Lodge & Hutz LLP

(57) ABSTRACT

The present invention relates to new yellow couplers of formula (I) for colour photographic materials

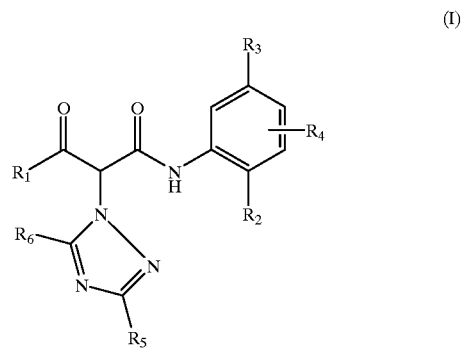

wherein
  $R_1$ represents alkyl or hetaryl,
  $R_2$ represents halogen, alkoxy, aryloxy,
  $R_3$ represents alkoxycarbonyl (—COOR'), carbamoyl (—CONHR'R"), urethane (—NHCOOR'),
  $R_4$ represents a substituent,
  $R_5$ represents alkyl or aryl, and
  $R_6$ represents hydroxy-(ethyloxy)$_n$, where n=1 to 2 and to a colour photographic material containing said couplers of formula (I).

11 Claims, No Drawings

ACETANILIDE COUPLERS

This invention relates to new yellow couplers for colour photograhic materials.

This invention further relates to a colour photographic material containing the new yellow couplers.

It is known that the blue-sensitive silver halide layer of a photographic material can be provided with 2-equivalent yellow couplers. Compared with the 4-equivalent couplers which were more frequently used hitherto, 2-equivalent couplers are characterised in that they only require about half as much silver halide for the formation of a given amount of dye. This has the advantage that the amount of silver halide in the material can be reduced, which results in thinner emulsion layers and thus at the same time results in better resolution and sharpness of the colour photographic material.

Amongst other factors, the photographic properties of a coupler are determined by the volatile group. There is a multiplicity of different volatile groups which are also known from the prior art for yellow couplers. Apart from halogens, some heterocyclic compounds which have already been used successfully. The volatile (groups should be both photographically inert and readily obtainable synthetically.

In addition to the volatile groups, however, the other substituents on the yellow coupler also have a considerable effect on the photographic properties. Thus benzoyl acetanilide couplers, which are very active as regards coupling, are usually employed in negative materials, for example. A disadvantage of this class of couplers, however, is the poor dark fading stability of dyes formed from these couplers.

In contrast, and as is known from the prior art, pivaloyl acetanilide couplers exhibit a high dye stability, but only exhibit a relatively low reactivity, which results in low colour density, film speed and gradation values. Therefore, pivaloyl acetanilide couplers are usually less suitable for use in CN films.

2-equivalent yellow couplers are known from DE-OS 2442703 which contain, as a volatile group, a 5-membered heterocyclic compound which is bonded via a nitrogen atom and which contains at least 2 nitrogen atoms. According to the disclosure of DE-OS 2442703, compounds such as these are characterised by a good shelf life and a high coupling capacity. However, it has been shown that, due to their sulphonamide substitution, compounds according to DE-OS 2442703 exhibit relatively broad half-band widths and there is a bathochromic shift in the absorption maximum.

In order to obtain couplers which satisfy current requirements, it is therefore necessary to achieve the optimum combination of the various substituents.

The underlying object of the present invention is to identify yellow couplers for photographic film materials which firstly exhibit a high dye stability, especially a high dark fading stability such as that which is described in the prior art for pivaloyl couplers in particular, and which at the same time exhibit good coupling kinetics, preferably such as those which are known from the prior art for benzoyl couplers. In particular, the yellow couplers according to the invention should have a half-band width which is as low as possible.

Surprisingly, it has been found that compounds of formula (I) exhibit both the good coupling kinetics which are required for use in photographic film materials, particularly CN film, and also at the same time exhibit good dark fading stability. Moreover, both the couplers themselves and the dyes formed therefrom are distinguished by their good tropical stability. In addition, the couplers according to the invention exhibit a low half-band width. Opaque display and reversal materials which contain compounds of formula (I) according to the invention are therefore characterised by their brilliant colour reproduction.

According to the present invention, the half-band width is to be understood as the band width of the absorption band at 50% of an absorption which is put at 100%.

According to the present invention, the tropical stability is to be understood as the stability at a temperature in the region of 35° C. and at a relative atmospheric humidity in the region of 90%.

The present Application relates to new yellow couplers of formula (I),

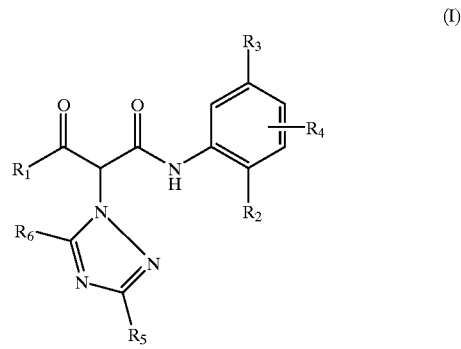

wherein
$R_1$ represents alkyl or hetaryl,
$R_2$ represents halogen, alkoxy, aryloxy,
$R_3$ represents alkoxycarbonyl (—COOR'), carbamoyl (—CONHR'R"), urethane (—NHCOOR'),
$R_4$ represents a substituent,
$R_5$ represents alkyl or aryl and
$R_6$ represents hydroxy-(ethyloxy)$_n$, where n=1 to 2.

Alkyl in the sense of the present Application is to be understood to mean linear or branched, cyclic or straight chain, substituted or unsubstituted hydrocarbon groups, preferably alkyl groups containing 1 to 22 C atoms, particularly 1 to 6 C atoms. Open-chain groups which are particularly suitable include methyl, ethyl, n-propyl and n-butyl. Branched alkyl radicals which are especially suitable include 2-hexyl-decyl and 2-ethylhexyl radicals, and t-butyl in particular. The preferred cycloalkyl groups include cyclohexyl groups such as 4-t-butyl-cyclohexyl and 2.6-di-t-butyl-4-methylcyclolhexyl for example, and particularly cyclopropyl groups such as ethylcyclopropyl for example.

Unless defined otherwise, hetaryl in the sense of the present Application is to be understood to mean aromatic systems which contain at least one hetero atom. These systems can comprise both substituted and unsubstituted ring systems. Typical examples include pyridine, pyrimidine, pyrazine, oxazole, isoxazole, thiazole, 3,4-oxadiazole, 1,2,4-oxadiazole, imidazole, indole, 1,2,3-thiazole and 1,2,4-triazole. Indolyl is particularly preferred.

Halogen in the sense of the present Application is to be understood to mean fluorine, chlorine or bromine in particular. Chlorine is particularly preferred.

Alkoxy in the sense of the present Application is to be understood to mean substituents of formula OR in which R represents an alkyl radical with the meaning given above. Examples thereof include methoxy, ethoxy, propoxy or butoxy substituents.

Aryloxy in the sense of the present Application is to be understood to mean substituents of formula OR in which R represents an aryl radical corresponding to the definition given below. Examples of aryloxy groups include phenoxy or napthoxy substituents.

R' and R" can represent any alkyl radical such as those cited above, and preferably comprise linear or branched, saturated or unsaturated alkyl radicals containing 8 to 22, particularly 10 to 18 C atoms.

Unless defined otherwise, a substituent in the sense of the present Application comprises H, a halogen, particularly fluorine, chlorine or bromine and alkyl, alkoxy, acylamino, carbamoyl, alkoxycarbonyl, aryl, aryloxy, hetaryl and alkenyl substituents, as well as $CF_3$ or CN.

Aryl in the sense of the present Application is to be understood to mean aromatic hydrocarbon groups, preferably 5- or 6-membered ring systems which can be present as monocyclic ring systems or as condensed ring systems. These ring systems can comprise both substituted and unsubstituted ring systems. Phenyl and naphthyl groups are particularly preferred, for example.

$R_1$ preferably represents an alkyl group. Tert-butyl is particularly preferred. $R_2$ preferably represents a halogen, particularly Cl, or a methoxy group. $R_3$ preferably represents alkoxycarbonyl, carbamoyl or urethane entities which contain linear or branched hydrocarbons which preferably comprise 10 to 18 carbon atoms. The preferred substituents $R_4$ are F, Cl, Br, alkyl, alkoxy, acylamino, carbamoyl and alkoxycarbonyl. $R_4$ most preferably represents H. In one preferred embodiment, $R_5$ represents a linear, saturated alkyl radical, particularly a butyl radical, or an aryl radical, particularly phenyl.

The present invention further relates to a colour photographic silver halide material comprising at least one blue-sensitive silver halide emulsion layer containing at least one yellow coupler, at least one green-sensitive silver halide emulsion layer containing at least one magenta coupler, and at least one red-sensitive silver halide emulsion layer containing at least one cyan coupler, in which compounds of formula (I) are used as yellow couplers.

According to the invention, at least one compound of formula (I) is used in at least one of the blue-sensitive silver halide emulsion layers.

The colour photographic silver halide material according to the invention is distinguished in particular by its good dark fading stability and by its increased colour brilliance.

The present invention also relates to the use of compounds of formula (I) according to the invention as yellow couplers in colour photographic materials. Compounds of formula (I) according to the invention are preferably used in CN film materials.

Examples of compounds of formula (I) with $R_1$=t-$C_4H_9$; $R_4$=H and $R_6$=HOCH$_2$CH$_2$—O which are preferred according to the invention are given below.

| No. | $R_2$ | $R_3$ | $R_5$ |
|---|---|---|---|
| 1 | Cl | —CO$_2$C$_{12}$H$_{25}$ | phenyl |
| 2 | Cl | —CO$_2$C$_{12}$H$_{25}$ | n-C$_4$H$_9$ |
| 3 | Cl | —CO$_2$C$_{16}$H$_{33}$ | phenyl |
| 4 | Cl | —CO$_2$C$_{18}$H$_{37}$ | phenyl |
| 5 | Cl | —CO$_2$CH$_2$CH(C$_6$H$_{13}$)C$_8$H$_{17}$ | phenyl |
| 6 | Cl | —CONHC$_{12}$H$_{25}$ | phenyl |
| 7 | Cl | —CONHC$_{18}$H$_{37}$ | phenyl |
| 8 | Cl | —CON(CH$_3$)C$_{18}$H$_{37}$ | phenyl |
| 9 | Cl | —CO$_2$CH$_2$CH(C$_6$H$_{13}$)C$_8$H$_{17}$ | phenyl |

-continued

| No. | $R_2$ | $R_3$ | $R_5$ |
|---|---|---|---|
| 10 | Cl | —NHCO$_2$C$_{12}$H$_{25}$ | phenyl |
| 11 | Cl | —NHCO$_2$C$_{16}$H$_{33}$ | phenyl |
| 12 | OCH$_3$ | —NHCO$_2$C$_{12}$H$_{25}$ | phenyl |
| 13 | Cl | —NHCO$_2$C$_{12}$H$_{25}$ | n-C$_4$H$_9$ |
| 14 | Cl | —NHCO$_2$CH$_2$CH(C$_6$H$_{13}$)C$_8$H$_{17}$ | phenyl |
| 15 | OCH$_3$ | —NHCO$_2$C$_{12}$H$_{25}$ | n-C$_4$H$_9$ |
| 16 | OCH$_3$ | —NHCO$_2$CH$_2$CH(C$_6$H$_{13}$)C$_8$H$_{17}$ | phenyl |
| 17 | Cl | NHCO$_2$CH(CH$_3$)C$_{10}$H$_{21}$ | phenyl |

Further examples are:

18.

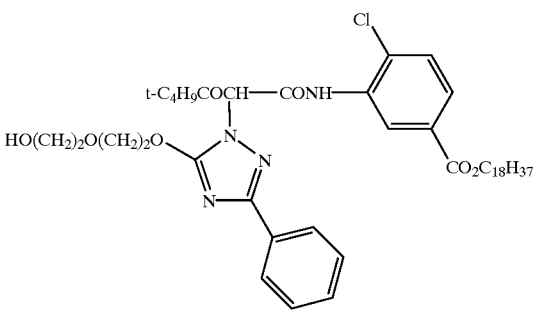

19.

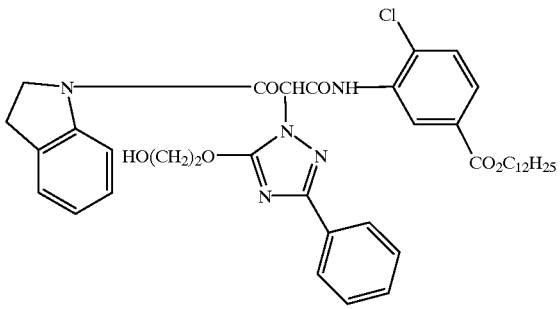

20.

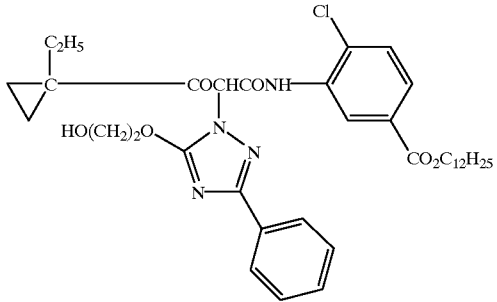

In one particularly preferred embodiment, the compounds of formula (I) according to the invention are used in photographic materials together with acylamino couplers of formula (II).

According to the present invention, at least one compound of formula (I) is used in at least one blue-sensitive silver halide layer and at least one compound of formula (II) is used in at least one green-sensitive silver halide emulsion layer.

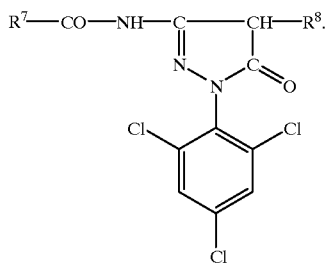

R⁷ and R⁸ in the above formula, independently of each other, can represent alkyl alkoxy, aryl, aryloxy, hetaryl, acylamino, carbamoyl or alkoxycarbonyl.

R⁷ preferably represents an aryl or alkyl group which itself can again be substituted by one or more of the aforementioned substituents.

R⁸ preferably represents hetaryl, particularly diazole or aryloxy.

The production of β-ketocarbanilide yellow couplers has been described many times in the past, e.g. in European Patent Applications 681215, 568196 and 475615, and also in Research Disclosure (April 1979) 18053. The coupler part of compounds (I) according to the invention can be produced, as described in the literature as follows:

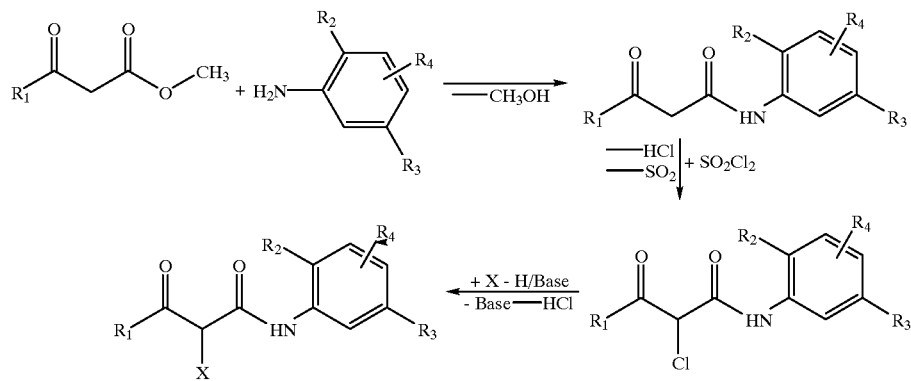

Volatile groups according to the invention can be obtained as follows, for example:

Method of Preparing 2-phenyl-5-(2-hydroxyethyloxy)-1,3,4-triazole

1. Phenyl Semicarbazone 111 g (1 mole) semicarbazide hydrochloride is neutralised with 136 g (1 mole) sodium acetate in 750 ml water and the batch is subsequently treated with 101 ml (1 mole) benzaldehyde. After washing with water and alcohol, the phenyl semicarbazone obtained is dried and processed further.

Yield: 149 g=91% theoretical. Melting point: 220° (decomposition).

2. 2-amino-5-phenyl-1,3,4-oxadiazole 123 g phenyl semicarbazone is placed in 900 ml acetic acid and 248 g anhydrous sodium acetate is added in portions with stirring. The batch is heated to 40° C. and a solution of 41 g bromine in 100 mil acetic acid is slowly added drop-wise. The batch is subsequently stirred for a further 1 hour. The reaction mixture is then stirred into water and the precipitate obtained is filtered off under suction, washed with water and dried.

Yield: 98 g=80% theoretical. Melting point: 244° (decomposition).

3,3-(2-hydroxyethyloxy-5-phenyl-1,2,4-triazole 158 g 2-amino-5-phenyl-1,3,4-oxadiazole are stirred with 154 g potassium hydroxide in 600 ml glycol at 90° C. for 4 hours. Thereafter the reaction mixture is allowed to cool to 50° C. and is acidified to pH 4 with about 200 ml of concentrated hydrochloric acid.

Water and excess glycol are subsequently distilled off under vacuum (5 mbar) at an internal temperature of 110° C. 1.8 l water are added to the glycol-free concentrate and the product is subsequently stirred for 3 hours at a temperature below 10° C. to promote crystallisation and the precipitated crystals are finally filtered off under suction. The product is purified by recrystallisation from 2:1 acetonitrile:ethyl acetate. Yield: 173 g=86% theoretical.

If different aldehydes are used in the 1st synthesis step, and if glycol is replaced by diethylene glycol, for example, in the last reaction step, this method of preparation results in other 3,5-substituted 1,2,4-triazoles and thus also results in the examples of couplers cited.

Synthesis of Yellow Coupler No. 1

50 g (0.1 mole) 2-chloro-5-dodecyloxycarbonyl-(2,2-chloro-pivaloyl) acetanilide were dissolved in 400 ml acetone at a temperature of 20° C. and 24.6 g (0.12 mole) 3-(2-hydroxyethyloxy)-5-phenyl-1,2,4-triazole were then added. 17.3 g (0.15 mole) tetramethylguanidine were added drop-wise with stirring. After the reaction was complete, the reaction mixture was stirred in iced water and the crude product was taken up in ethyl acetate and washed with dilute hydrochloric acid. Crystallisation occurred after/during stirring overnight. Yield: 43.5 g=65% theoretical, Melting point: 73° C.

The colour photographic material according to the invention can additionally contain compounds which are capable of releasing a development inhibitor, a development accelerator, a bleaching accelerator, a developer, a solvent for silver halides, a fogging agent or an anti-fogging agent, for example what are termed DIR hydroquinones or other compounds such as those which are described in U.S. Pat. Nos. 4,636,546, 4,345,024 and 4,684,604 and in DE-A 24 47 079, DE-A 25 15 213 and DE-A 31 45 640, or in EP-A 198 438. These compounds perform the same function as DIR, DAR or FAR couplers, except that they do not form coupling products.

High molecular weight colour couplers are described in DE-C 1 297 417, DE-A 24 07 569, DE-A 31 48 125, DE-A 32 17 200, DE-A 33 20 079, DE-A 33 24 932, DE A 33 31

743, DE-A 33 40 376, EP-A 27 284 and U.S. Pat. No. 4,080,211, for example. High molecular weight colour couplers are generally produced by the polymerisation of ethylenically unsaturated colour coupler monomers. They can also be obtained by addition polymerisation or condensation polymerisation, however.

The colour couplers according to the invention can be incorporated in silver halide emulsion layers can by firstly preparing a solution or a dispersion of the compound concerned and then adding the casting solution for the layer in question. The choice of a suitable solvent or dispersion medium depends on the solubility of the compound.

Methods of introducing compounds which are substantially insoluble in water by grinding processes are described in DE-A 26 09 741 and DE-A 26 09 742, for example Hydrophobic compounds can also be incorporated into the casting solution by employing high boiling solvents which are termed oil-formers. Corresponding methods are described in U.S. Pat. Nos. 2,322,027, 2,801,170 and EP-A 0 043 037, for example. Instead of low molecular weight oil-formers, oligomers or polymers which exhibit suitable solvent properties can also be used. The couplers according to the invention are preferably of a hydrophobic structure.

The compounds can also be introduced into the casting solution in the form of what are termed filled latices. Reference is made in this respect, for example, to DE-A 25 41 230, DE-A 25 41 274, DE-A 28 35 856, EP-A 0 014 921, EP-A 0 069 671, EP-A 0 130 115 and U.S. Pat. No. 4,291,113. The diffusion-resistant incorporation of anionic, water-soluble compounds (e.g. of couplers or dyes) can also be effected with the aid of cationic polymers termed polymeric mordants.

Examples of suitable oil-formers include alkyl phthalates, esters of phosphoric acid, esters of phosphonic acid, esters of citric acid, esters of lactic acid, esters of benzoic acid, esters of fatty acids, amides, alcohols, phenols, sulphonamides, aniline derivatives and hydrocarbons.

Examples of colour photographic materials include colour negative films, colour reversal films and colour positive films. A review of typical colour photographic materials and of preferred forms thereof and processing procedures therefor is given in Research Disclosure 37038 (February 1995).

Photographic materials consist of a support on which at least one light-sensitive silver halide emulsion layer is deposited. Thin films and foils are particularly suitable as supports. A review of support materials and of the auxiliary layers which are deposited on the front and back thereof is given in Research Disclosure 37254, Part 1 (1995), page 285.

Colour photographic materials usually contain at least one red-sensitive, at least one green-sensitive and at least one blue-sensitive silver halide emulsion layer, and optionally contain intermediate layers and protective layers also.

Depending on the type of photographic material, these layers may be arranged differently. This will be illustrated for the most important products:

Colour photographic films such as colour negative films and colour reversal films comprise, in the following sequence on their support: 2 or 3 red-sensitive, cyan-coupling silver halide emulsion layers, 2 or 3 green-sensitive, magenta coupling silver halide emulsion layers, and 2 or 3 blue-sensitive, yellow-coupling silver halide emulsion layers. The layers of identical spectral sensitivity differ as regards their photographic speed, wherein the less sensitive partial layers are generally disposed nearer the support than are the more highly sensitive partial layers.

A yellow filter layer is usually provided between the green-sensitive and blue-sensitive layers, to prevent blue light from reaching the layers underneath.

The options for different layer arrangements and their effects on photographic properties are described in J. Inf. Rec. Mats., 1994, Vol. 22, pages 183–193.

Departures from the number and arrangement of the light-sensitive layers may be effected in order to achieve defined results. For example, all the high-sensitivity layers may be combined to form a layer stack and all the low-sensitivity layers may be combined to form another layer stack in a photographic film, in order to increase the sensitivity (DE 2530645).

The essential constituents of the photographic emulsion layer are binders, silver halide grains and colour couplers.

Information on suitable binders is given in Research Disclosure 37254, Part 2 (1995), page 286.

Information on suitable silver halide emulsions their production, ripening, stabilisation and spectral sensitisation, including suitable spectral sensitisers, is given in Research Disclosure 36544, (September 1994), in Research Disclosure 37254, Part 3 (1995), page 286, and in Research Disclosure 37038, Part XV (1995), page 89.

Photographic materials which exhibit camera-sensitivity usually contain silver bromide-iodide emulsions, which may also optionally contain small proportions of silver chloride. These materials preferably comprise what are termed tab grain crystals of a defined crystalline form which are characterised by their volume to surface ratio. In the sense of the present invention, tab grain crystals with an aspect ratio from 5 to 20 are preferably used.

Photographic emulsions can be spectrally sensitised using methine dyes or other dyes. Cyanin dyes, merocyanin dyes and complex merocyanin dyes are particularly suitable dyes. Compounds of this type, particularly merocyanins, can also be used as stabilisers.

A review of polymethine dyes which are suitable as spectral sensitisers, of suitable combinations thereof, and of combinations which exhibit a super-sensitising effect in particular, is given in Research Disclosure 17643 (1978), Section IV, and in Research disclosure 18716 (1979), page 648 (right-hand column) to page 649 (right-hand column).

Other substances which can be used as red sensitisers include pentamethine cyanins which contain naphthothiazole, naphthoxazole or benzthiazole as basic terminal groups, which are substituted with halogen, methyl or methoxy groups in particular and which can be bridged by a 9,11-alkylene, particularly by 9,11-neopentylene, such as those described in GB 604 217 and BE 660 948. The N,N'-substituents can also be $C_4$–$C_8$ alkyl groups, as described in EP 0 532 042. In addition, the methine chain can also comprise substituents, as disclosed in EP 0 532 042. Pentamethines which only contain one methyl group on their cyclohexene ring can also be used, such as those described in EP 0 532 042. As described in BE 660 948, the red sensitiser can be super-sensitised and stabilised by the addition of heterocyclic mercapto compounds.

In addition, the red-sensitive layer can be spectrally sensitised between 390 and 590 nm, preferably at 500 nm in order thus to effect better differentiation between shades of red in accordance with EP 0 304 297, U.S. Pat. Nos. 806,460 and 5,084,374.

Compounds of this type, particularly merocyanins, can also be used as stabilisers.

Spectral sensitisers can be added in dissolved form or as a dispersion to the photographic emulsion. Both solutions and dispersions may also contain additives such as wetting agents or buffers, for example.

The spectral sensitiser or a combination of spectral sensitisers can be added before, during or after the preparation of the emulsion.

Information on customary colour couplers is to be found in Research Disclosure 37254, Part 4 (1995), page 288, and in Research Disclosure 37038, Part II (1995), page 80. The maximum absorption of the dyes formed from the couplers and from the colour developer oxidation product preferably falls within the following ranges: yellow couplers 430 to 460 nm, magenta couplers 540 to 560 nm, cyan couplers 630 to 700 nm.

In order to improve sensitivity, granularity, sharpness and colour separation, compounds are frequently used in colour photographic films which on reaction with the developer oxidation product release compounds which are photographically active, e.g. DIR couplers, which release a development inhibitor.

Information on compounds such as these, particularly couplers, is to be found in Research Disclosure 37254, Part 5 (1995), page 290, and in Research Disclosure 37038, Part XIV (1995), page 86.

The colour couplers, which are mostly hydrophobic, and other hydrophobic constituents of the layers also, are usually dissolved or dispersed in high-boiling organic solvents. These solutions or dispersions are then emulsified in an aqueous binder solution (usually a gelatine solution), and after the layers have been dried are present as fine droplets (0.05 to 0.8 μm diameter) in the layers.

Suitable high-boiling organic solvents, methods of introduction into the layers of a photographic material, and other methods of introducing chemical compounds into photographic layers, are described in Research Disclosure 37254, Part 6 (1995), page 292.

The light-insensitive intermediate layers which are generally disposed between layers of different spectral sensitivity may contain media which prevent the unwanted diffusion of developer oxidation products from one light-sensitive layer into another light-sensitive layer which has a different spectral sensitivity.

Suitable compounds (white couplers, scavengers or DOP scavengers) are described in Research Disclosure 37254, Part 7 (1995), page 292, and in Research Disclosure 37038, Part III (1995), page 84.

The photographic material may additionally contain compounds which absorb UV light, brighteners, spacers, filter dyes, formalin scavengers light stabilisers, anti-oxidants, $D_{Min}$ dyes, additives for improving the dye-, coupler- and white stability and to reduce colour fogging, plasticisers (latices), biocides and other substances.

Suitable compounds are given in Research Disclosure 37254, Part 8 (1995), page 292, and in Research Disclosure 37038, Parts IV, V, VI, VII, X, XI and XIII (1995), pages 84 et seq.

The layers of colour photographic materials are usually hardened, i.e. the binder used, preferably gelatine, is crosslinked by suitable chemical methods.

Suitable hardener substances are described in Research Disclosure 37254, Part 9 (1995) page 294, and in Research Disclosure 37038, Part XII (1995), page 86.

After image-by-image exposure, colour photographic materials are processed by different methods corresponding to their character. Details on the procedures used and the chemicals required therefor are published in Research Disclosure 37254, Part 10 (1995), page 294, and in Research Disclosure 37038, Parts XVI to XXIII (1995), page 95 et seq., together with examples of materials.

EXAMPLES

Example 100

A colour photographic recording material for colour negative colour development was produced by depositing the following layers in the given sequence on a transparent film base of cellulose triacetate. The quantitative data are given with respect to 1 m² in each case. The corresponding amounts of $AgNO_3$ are quoted for silver halide deposition. The silver halides were stabilised with 0.5 g 4-hydroxy-6-methyl-1,3,3a,7-tetraazaindene per mole $AgNO_3$.

| | |
|---|---|
| | 1st layer (anti-halo layer) |
| 0.3 g | black colloidal silver |
| 1.2 g | gelatine |
| 0.3 g | UV absorber UV-1 |
| 0.2 g | DOP (developer oxidation product) - scavenger SC-1 |
| 0.02 g | tricresyl phosphate (TCP) |
| | 2nd layer (low red-sensitivity layer) |
| 0.7 g | $AgNO_3$ of an AgBrI emulsion spectrally sensitized to red, 4 mole-% iodide, average grain diameter 0.42 μm |
| 1 g | gelatine |
| 0.35 g | colourless coupler C-1 |
| 0.05 g | colourless coupler RC-1 |
| 0.03 g | colourless coupler YC-1 |
| 0.36 g | TCP |
| | 3rd layer (medium red-sensitivity layer) |
| 0.8 g | $AgNO_3$ of an AgBrI emulsion spectrally sensitized to red, 5 mole-% iodide, average grain diameter 0.53 μm |
| 0.6 g | gelatine |
| 0.15 g | colourless coupler C-2 |
| 0.03 g | coloured coupler RC-1 |
| 0.02 g | DIR coupler D-1 |
| 0.18 g | TCP |
| | 4th layer (high red-sensitivity layer) |
| 1 g | $AgNO_3$ of an AgBrI emulsion spectrally sensitized to red, 6 mole-% iodide, average grain diameter 0.85 μm |
| 1 g | gelatine |
| 0.1 g | colourless coupler C-2 |
| 0.005 g | DIR coupler D-2 |
| 0.11 g | TCP |
| | 5th layer (intermediate layer) |
| 0.8 g | gelatine |
| 0.07 g | DOP scavenger SC-2 |
| 0.06 g | aluminium salt of aurin tricarboxylic acid |
| | 6th layer (low green-sensitivity layer) |
| 0.7 g | $AgNO_3$ of an AgBrI emulsion spectrally sensitized to green, 4 mole-% iodide, average grain diameter 0.35 μm |
| 0.8 g | gelatine |
| 0.22 g | colourless coupler M-1 |
| 0.065 g | coloured coupler YM-1 |
| 0.02 g | DIR coupler D-3 |
| 0.2 g | TCP |
| | 7th layer (medium green-sensitivity layer) |
| 0.9 g | $AgNO_3$ of an AgBrI emulsion spectrally sensitized to green, 4 mole-% iodide, average grain diameter 0.50 μm |
| 1 g | gelatine |
| 0.16 g | colourless coupler M-1 |
| 0.04 g | coloured coupler YM-1 |
| 0.015 g | DIR coupler D-4 |
| 0.14 g | TCP |

-continued

8th layer (high green-sensitivity layer)

| | |
|---|---|
| 0.6 g | $AgNO_3$ of an AgBrI emulsion spectrally sensitized to green, 6 mole-% iodide, average grain diameter 0.70 μm |
| 1.1 g | gelatine |
| 0.05 g | colourless coupler M-1 |
| 0.01 g | coloured coupler YM-2 |
| 0.02 g | DIR coupler D-5 |
| 0.08 g | TCP |

9th layer (yellow filter layer)

| | |
|---|---|
| 0.09 g | yellow dye GF-1 |
| 1 g | gelatine |
| 0.08 g | DOP scavenger SC-2 |
| 0.26 g | TCP |

10th layer (low blue-sensitivity layer)

| | |
|---|---|
| 0.3 g | $AgNO_3$ of an AgBrI emulsion spectrally sensitized to blue, 6 mole-% iodide, average grain diameter 0.44 μm |
| 0.5 g | $AgNO_3$ of an AgBrI emulsion spectrally sensitized to blue, 6 mole-% iodide, average grain diameter 0.50 μm |
| 1.9 g | gelatine |
| see Example | colourless coupler Y-1 |
| 0.037 g | DIR coupler D-6 |
| 0.6 g | TCP |

11th layer (high blue-sensitivity layer)

| | |
|---|---|
| 0.6 g | $AgNO_3$ of an AgBrI emulsion spectrally sensitized to blue, 7 mole-% iodide, average grain diameter 0.95 μm |
| 1.2 g | gelatine |
| see Example | colourless coupler Y-1 |
| 0.006 g | DIR coupler D-7 |
| 0.11 g | TCP |

12th layer (micrate layer)

| | |
|---|---|
| 0.1 g | $AgNO_3$ of a micrate-AgBrI emulsion, 0.5 mole-% iodide, average grain diameter 0.06 μm |
| 1 g | gelatine |
| 0.004 mg | $K_2[PdCl_4]$ |
| 0.4 g | UV absorber UV-2 |
| 0.3 g | TCP |

13th layer (protective and hardener layer)

| | |
|---|---|
| 0.25 g | gelatine |
| 0.75 g | hardener H-1 |

After hardening, the layer structure as a whole exhibited a swelling factor <3.5.

Substances used in Example 1:

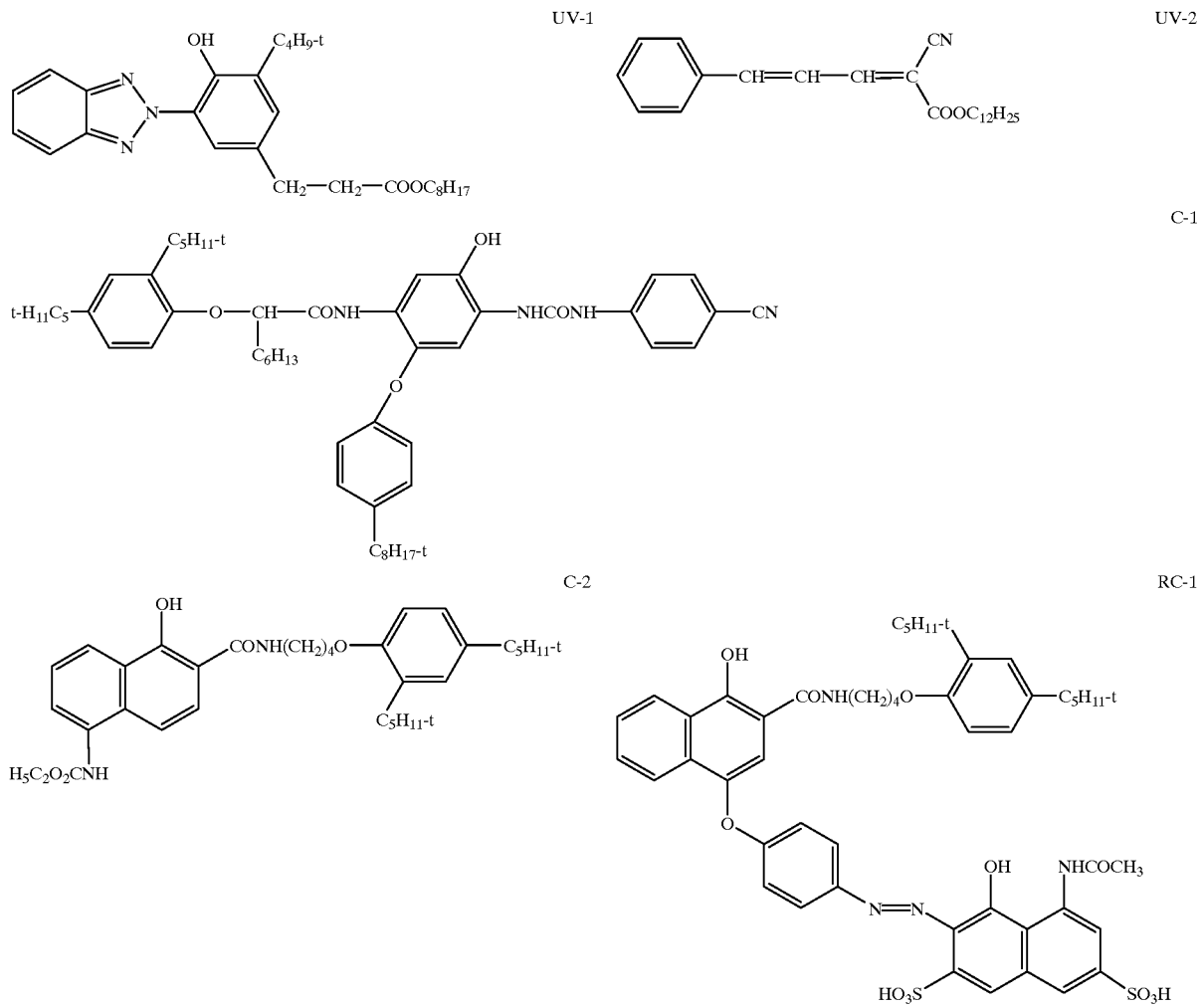

-continued
YC-1
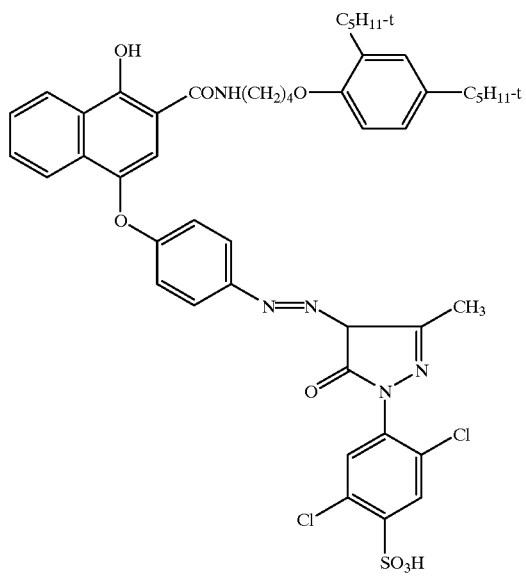
M-1
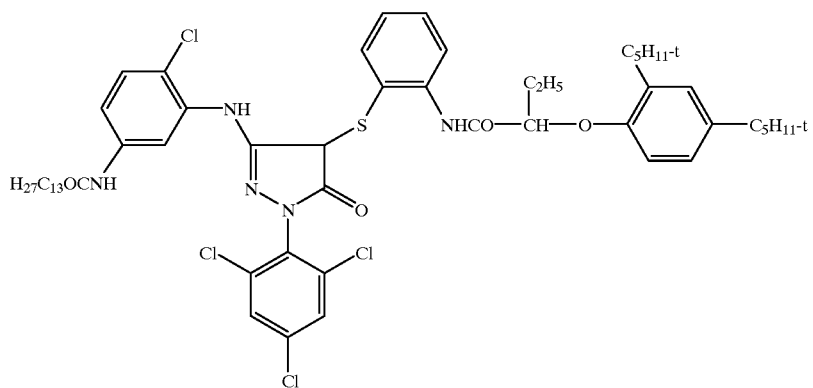
M-2
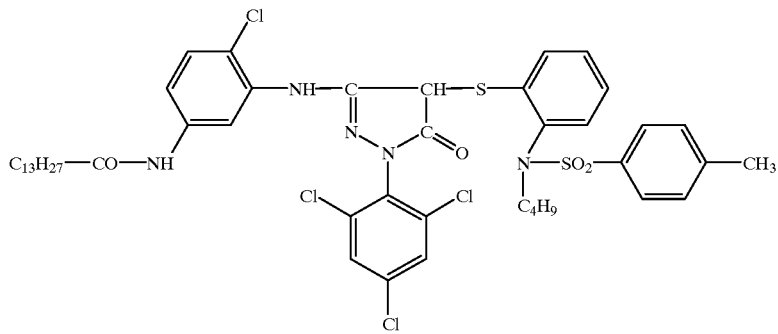
M-3
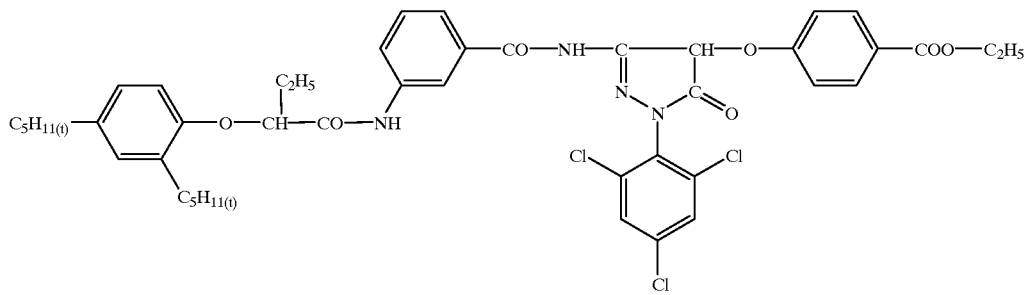

M-4
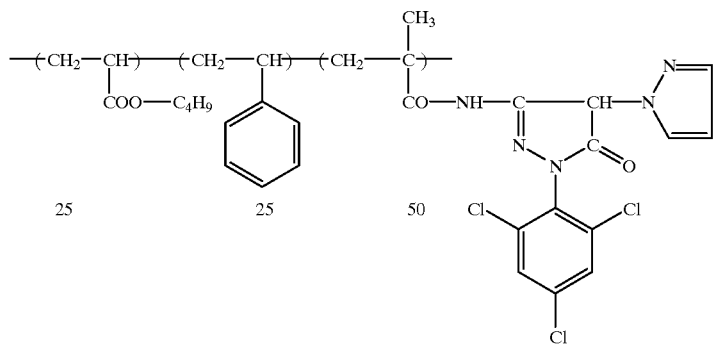
YM-1
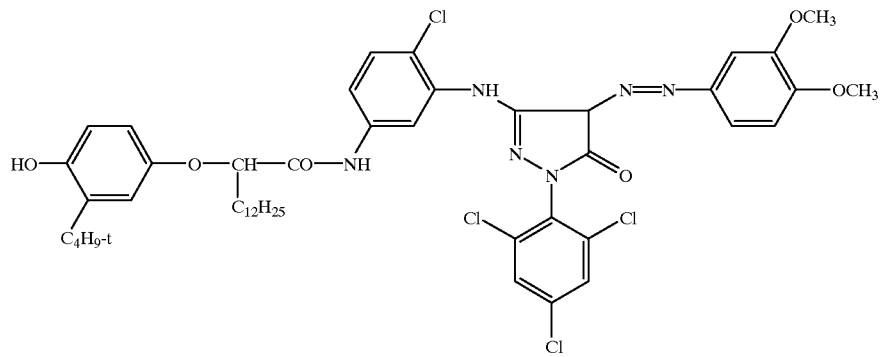
YM-2
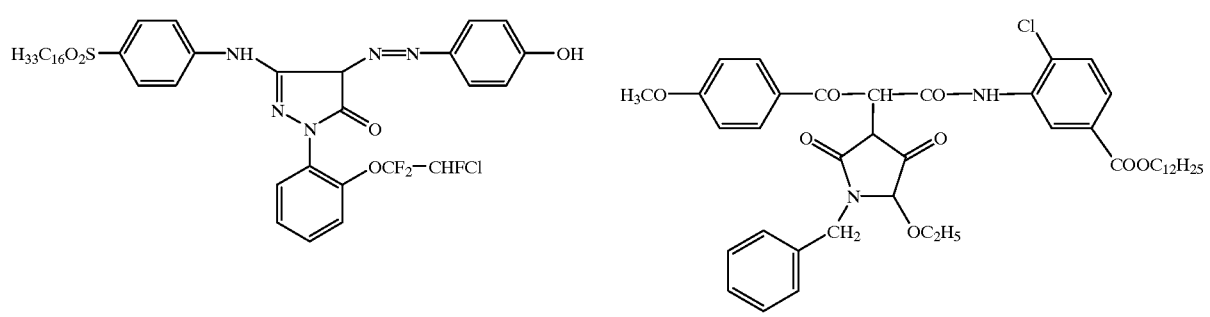
Y-1
Y-2
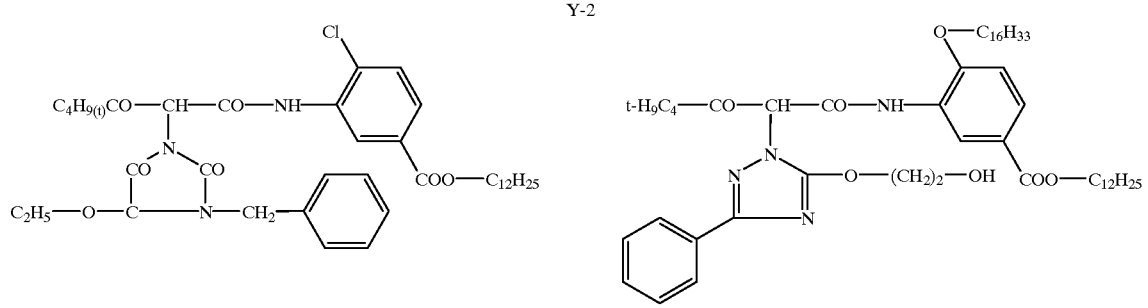
Y-3

-continued
D-1
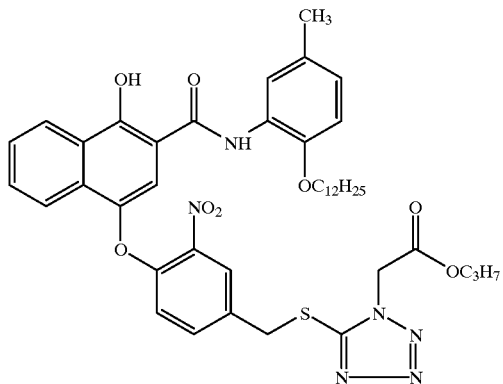
D-2
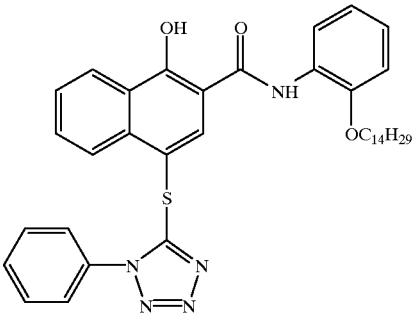
D-3
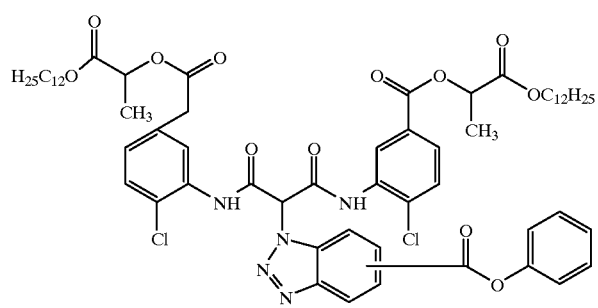
D-4
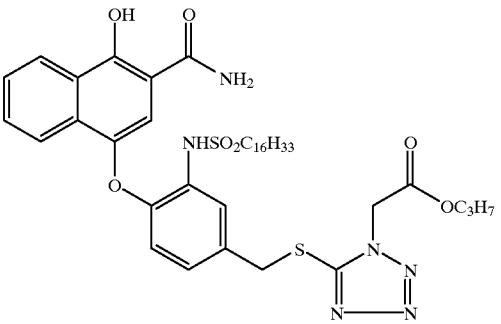
D-5
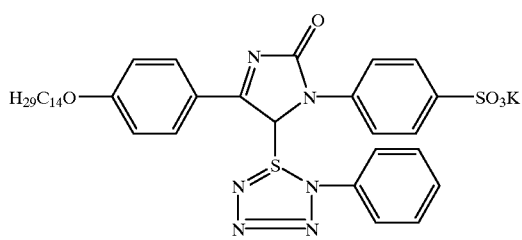
D-6
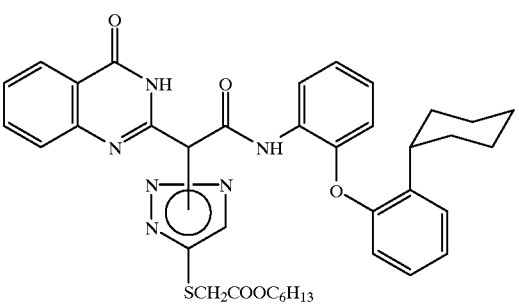
D-7
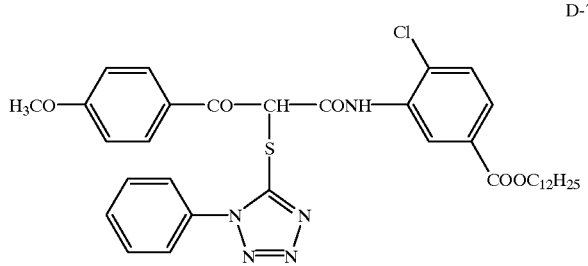
SC-1
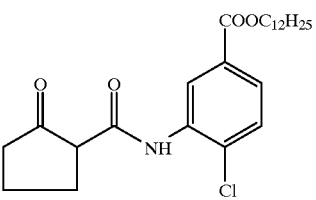
SC-2
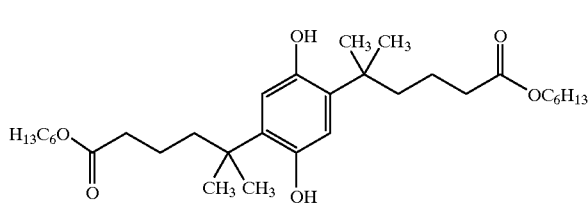
GF-1
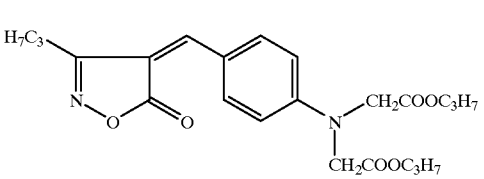

H-1

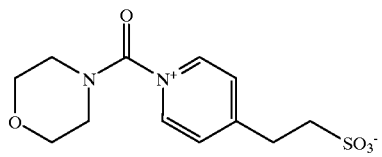

Examples 101–106 differed from Example 100 in that other comparison couplers from the prior art, and couplers according to the invention, were used instead of comparison coupler Y-1 in the 10th and 11th layers. The amounts and types of the couplers used are given in Table 1.

TABLE 1

| Example | Coupler [mmole/m²] in layer 10 | Coupler [mmole/m²] in layer 11 | |
|---|---|---|---|
| 100 | Y-1 [1, 4] | Y-1 [0.13] | comparison |
| 101 | Y-2 [2, 2] | Y-2 [0.2] | comparison |
| 102 | Y-3 [2, 2] | Y-3 | comparison |
| 103 | 1 [2, 2] | 1 | according to the invention |
| 104 | 2 [2, 2] | 2 | according to the invention |
| 105 | 5 [2, 2] | 5 | according to the invention |
| 106 | 9 [2, 2] | 9 | according to the invention |

Y-3 is coupler 20 cited in Example 1 of DE-OS 2442703.

After exposing a neutral wedge, the materials produced were processed as described in the British Journal of Photography, 974, pages 597 and 598. The sensitometry results obtained are given in Table 2.

It can clearly be seen that the couplers according to the invention resulted in a more favourable sensitometry than that of the comparison couplers. Since the couplers according to the invention and couplers Y-2 and Y-3 are what are termed pivaloyl yellow couplers, the dyes of which have a lower absorption coefficient than that of comparison coupler 1, it is understandable that larger molar amounts per m² have to be used.

The same material was also exposed behind a Status M blue filter. After the same type of development to that described above, spectral measurements were made on the developed material. It can clearly be seen that the couplers according to the invention exhibit an absorption, which is more favourable for film materials, of about 450 nm and/or a lesser half-band width.

TABLE 2

| Example | γ- | D max | Rel. blue sensitivity | HBW [nm] | λ max [nm] |
|---|---|---|---|---|---|
| 100 | 0.54 | 2.84 | 100 | 86 | 452 |
| 101 | 0.38 | 2.20 | 90 | 85 | 450 |
| 102 | 0.60 | 3.01 | 98 | 94 | 458 |
| 103 | 0.64 | 3.03 | 117 | 85 | 451 |
| 104 | 0.68 | 3.12 | 123 | 85 | 450 |
| 105 | 0.59 | 2.98 | 112 | 86 | 452 |
| 106 | 0.61 | 3.01 | 114 | 85 | 452 |

Example 200

This example differed from Example 100 in that a different magenta coupler (as detailed in Table 3) was used in the 6th, 7th and 8th layers. In the other examples, namely Examples 201–207. other yellow coupler/magenta coupler combinations were used, as given in the Table. The couplers used are listed in Table 3. 12 sensitometer strips were exposed in each case as described in Example 100, and were processed in a Hostert DD20 experimental development machine without a supply ol nitrogen pulses in the developer. In a second series of tests, 12 sensitometer strips were again developed, with a pulsed stream of nitrogen being blown in for 8 seconds with a pause of 2 seconds. The relative magnitudes of the development scatter ellipses which were obtained from a trilinear colour diagram are given in the last column of Table 3. In this series of tests a combination of the pivaloyl couplers according to the invention with acylaminopyrazolone couplers M-3 and M-4 proved particularly favourable.

TABLE 3

| Ex. | Coupler [mmole/m²] in layer 6 | coupler [mmole/m² in layer 7 | coupler [mmole/m²] in layer 8 | coupler [mmole/m²] in layer 10 | coupler [mmole/m²] in layer 11 | Relative magnitude of the scatter ellipse | |
|---|---|---|---|---|---|---|---|
| 100 | M-1[0.215] | M-1[0.156] | M-1[0.05] | Y 1 [1.4] | Y-1 [0.1] | 5.42 | comparison |
| 200 | M-2[0.30] | M-2[0.21] | M-2[0.07] | " | " | 6.18 | comparison |
| 201 | M-3[0.35] | M-3[0.17] | M-3[0.06] | " | " | 4.75 | comparison |
| 202 | M-21[0.30] | M-2[0.21] | M-2[0.07] | 1 [2.2] | 1 [0.2] | 2.23 | according to the invention |
| 203 | M-3[0.35] | M-3[0.1] | M-3[0.06] | 2 " | 2 " | 1.64 | according to the invention |
| 204 | M-4[0.25] | M-4[0.175] | M4[0.057] | 1 " | 1 " | 1.20 | according to the invention |
| 205 | M-4 " | M-4 " | M4 " | 5 " | 5 " | 1.25 | according to the invention |
| 206 | M-4 " | M-4 " | M4 " | 9 " | 9 " | 1.23 | according to the invention |
| 207 | M-4 " | M-4 " | M-4 " | Y-1 [1.4] | Y-1 [0.13] | 5.16 | comparison |

What is claimed is:

1. A yellow coupler of formula (I)

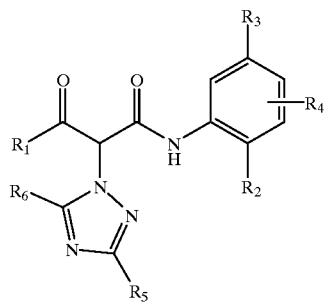

wherein
- $R_1$ represents alkyl having from 1 to 22 carbon atoms,
- $R_2$ represents halogen, alkoxy having from 1 to 22 carbon atoms or aryloxy of the formula OR''' in which R''' is a phenyl or naphthyl group,
- $R_3$ represents alkoxycarbonyl (—COOR), carbamoyl (—CONHRR') or urethane (—NHCOOR), wherein R and R' are identical or different and are an alkyl having from 1 to 22 carbon atoms,
- $R_4$ represents hydrogen, halogen, alkoxy having from 1 to 22 carbon atoms, $CF_3$, CN, phenyl, naphthyl or an alkyl having from 1 to 22 carbon atoms,
- $R_5$ represents alkyl having from 1 to 22 carbon atoms phenyl or naphthyl and
- $R_6$ represents hydroxy-(ethyloxy)$_n$, where n=1 to 2.

2. The yellow coupler according to claim 1, wherein $R_4$ represents alkyl having from 1 to 22 carbon atoms.

3. Yellow coupler according to claim 1, wherein $R_4$ represents H.

4. Yellow coupler according to claim 1, wherein $R_1$ represents tertiary butyl.

5. The yellow coupler as claimed in claim 3, wherein $R_1$ is t-$C_4H_9$ and $R_4$ is hydrogen.

6. The yellow coupler as claimed in claim 1, wherein n is 1 and $R_4$ is hydrogen.

7. The yellow coupler according to claim 5, wherein n is 1 and $R_2$ is Cl or $OCH_3$.

8. The yellow coupler as claimed in claim 6, wherein $R_5$ is phenyl or $C_4H_9$.

9. The yellow coupler as claimed in claim 7, wherein $R_5$ is phenyl.

10. The yellow coupler as claimed in claim 1, wherein R and R' are identical or different and are an alkyl with 8 to 22 carbon atoms.

11. The yellow coupler as claimed in claim 1, wherein R and R' are identical or different and are an alkyl with 10 to 18 carbon atoms.

* * * * *